US008015887B2

(12) United States Patent
Ayliffe et al.

(10) Patent No.: US 8,015,887 B2
(45) Date of Patent: Sep. 13, 2011

(54) INSTRUMENTED PIPETTE TIP

(75) Inventors: Harold E. Ayliffe, Woodinville, WA (US); Curtis S. King, Kirkland, WA (US)

(73) Assignee: E I Spectra, LLC

( * ) Notice: Subject to any disclaimer, the term of this patent is extended or adjusted under 35 U.S.C. 154(b) by 0 days.

(21) Appl. No.: 12/679,548

(22) PCT Filed: Sep. 26, 2008

(86) PCT No.: PCT/US2008/011205
§ 371 (c)(1),
(2), (4) Date: Mar. 23, 2010

(87) PCT Pub. No.: WO2009/045343
PCT Pub. Date: Apr. 9, 2009

(65) Prior Publication Data
US 2010/0199788 A1    Aug. 12, 2010

Related U.S. Application Data

(60) Provisional application No. 60/995,752, filed on Sep. 29, 2007.

(51) Int. Cl.
*B01L 3/02* (2006.01)
(52) U.S. Cl. .................................. 73/864.11
(58) Field of Classification Search .............. 73/864.01, 73/864.11, 863.01
See application file for complete search history.

(56) References Cited

U.S. PATENT DOCUMENTS

| | | | |
|---|---|---|---|
| 2,656,508 A | 10/1953 | Coulter | |
| 3,910,702 A | 10/1975 | Corll | |
| 4,130,754 A | 12/1978 | Fosslien | |
| 4,164,870 A | 8/1979 | Scordato et al. | |
| 4,488,814 A | 12/1984 | Johnson | |
| 4,873,875 A | 10/1989 | Cork | |
| 5,376,878 A | 12/1994 | Fisher | |
| 5,516,564 A | 5/1996 | Root et al. | |
| 5,695,092 A | 12/1997 | Schrandt | |
| 6,169,394 B1 | 1/2001 | Frazier et al. | |
| 6,285,807 B1 | 9/2001 | Walt et al. | |
| 6,370,942 B1 * | 4/2002 | Dunfee et al. | 73/37 |
| 6,382,228 B1 | 5/2002 | Cabuz et al. | |
| 6,396,584 B1 | 5/2002 | Taguchi et al. | |
| 6,426,615 B1 | 7/2002 | Mehta | |
| 6,437,551 B1 | 8/2002 | Krulevitch et al. | |
| 6,440,725 B1 | 8/2002 | Pourahmadi et al. | |

(Continued)

FOREIGN PATENT DOCUMENTS

WO    WO 2005121780 A2 * 12/2005

*Primary Examiner* — Hezron E Williams
*Assistant Examiner* — Tamiko Bellamy
(74) *Attorney, Agent, or Firm* — Brian C. Trask

(57) ABSTRACT

An improved pipette tip (100) including an elongate body stretching between a proximal end (116) and a distal end (114). The body (112) is typically made from a plurality of layers (e.g. 130, 132, 134, 136, 138) configured and arranged to provide a fluid path extending from the distal end toward the proximal end. The improved pipette tip (100) includes a sensor component disposed to electrically interrogate fluid flowing along the fluid path. An operable sensor component includes an electrode (e.g. 154, 192) that is disposed in the fluid path to contact fluid therein. A pipette tip (100) may be embodied to: count particles, verify sample integrity (e.g. freedom from bubbles), monitor sample flow rate, and confirm an inspired volume, among other uses.

19 Claims, 10 Drawing Sheets

U.S. PATENT DOCUMENTS

| | | |
|---|---|---|
| 6,454,945 B1 | 9/2002 | Weigl et al. |
| 6,461,808 B1 * | 10/2002 | Bodner et al. .................... 435/4 |
| 6,488,896 B2 | 12/2002 | Weigl et al. |
| 6,656,431 B2 | 12/2003 | Holl et al. |
| 6,663,353 B2 | 12/2003 | Lipscomb et al. |
| 6,703,819 B2 | 3/2004 | Gascoyne et al. |
| 6,703,849 B2 | 3/2004 | Ishioka et al. |
| 6,794,877 B2 | 9/2004 | Blomberg et al. |
| 7,223,371 B2 | 5/2007 | Hayenga et al. |
| 7,413,710 B2 * | 8/2008 | Lisec et al. .................... 422/100 |
| 2002/0061260 A1 | 5/2002 | Husar |
| 2002/0086431 A1 * | 7/2002 | Markham et al. ............... 436/63 |
| 2002/0117517 A1 | 8/2002 | Unger et al. |
| 2003/0180965 A1 | 9/2003 | Yobas et al. |
| 2004/0151629 A1 | 8/2004 | Pease et al. |
| 2005/0054078 A1 | 3/2005 | Miller et al. |
| 2005/0118705 A1 | 6/2005 | Rabbitt et al. |
| 2006/0073609 A1 | 4/2006 | Shimizu |
| 2009/0272179 A1 * | 11/2009 | Ayliffe ........................ 73/61.71 |

* cited by examiner

INSTRUMENTED PIPETTE TIP

PRIORITY CLAIM

This application claims the benefit under 35 U.S.C. 119(e) of the filing date of U.S. Provisional Patent Application Ser. No. 60/995,752, filed Sep. 29, 2007, for "INSTRUMENTED PIPETTE TIP", the entire contents of which are incorporated herein by this reference.

TECHNICAL FIELD

This invention relates to devices for extracting a fluid sample from a bulk fluid container while electrically interrogating the sample.

BACKGROUND

Handheld pipettes, which are used for precision fluid volume measurement and delivery, are some of the most common and widely-used laboratory tools available to scientists today. Nearly all low-volume fluid handling of biological and chemical liquid samples rely on their ease of use, precision and repeatability to ensure proper, consistent experimental processing. Commercial pipettes are available in a wide variety of fixed and adjustable volumes. When used in large-scale, high-throughput testing, commercially available pipettes are often multiple-channel, allowing for precise fluid metering of up to 12 different samples, simultaneously, with the single push of a button. Typical pipette instruments rely on positive displacement systems (e.g. either a manually operated plunger system, or an electronic pump) to generate the pressure required to urge a specified fluid volume into, or out of, a disposable pipette tip. Once the sample is ejected, the pipette tip is discarded. State-of-the-art pipette instruments are capable of accurately metering fluid volumes of less than 1 mL, and employ servo pumps for volume control and fluid metering. Digital displays with integrated electronic controls improve the pipette instrument's ease of use for the operator.

In the laboratory, pipettes are found in wet bench environments and are used in countless fluid-metering applications ranging from fluid mixing to sample isolation and preparation. In experimental cell biology, pipettes are routinely used to isolate small volume suspensions of cells in culture. In one of the most common procedures, manually counting (under microscope observation) a small portion of the cells in a precisely metered volume allows a user to make population and cell viability estimates for the entire volume of cells in culture. Unfortunately, counting cells under a microscope using this approach is very time and resource intensive, and count accuracy depends wholly on the number of cells a user is willing to actually count in the given volume.

Pioneering work in particle detection by measuring impedance deviation caused by particles flowing through a small aperture between two containers of electrically conductive fluids is disclosed in U.S. Pat. No. 2,656,508 to W. H, Coulter. The inventor's name is now associated with the principle of particles causing a change in electric impedance as they occlude a portion of the aperture. Since publication of his patent, considerable effort has been devoted to developing and refining sensing devices operating under the Coulter principle. Relevant US patents include U.S. Pat. No. 5,376,878 to Fisher, U.S. Pat. No. 6,703,819 to Gascoyne et al., U.S. Pat. No. 6,437,551 to Krulevitch et al., U.S. Pat. No. 6,426,615 to Mehta, U.S. Pat. No. 6,169,394 to Frazier et al., U.S. Pat. Nos. 6,454,945 and 6,488,896 to Weigl et al., U.S. Pat. No. 6,656,431 to Holl et al., and U.S. Pat. No. 6,794,877 to Blomberg et al. All of the above-referenced documents are hereby incorporated by reference, as though set forth herein in their entireties, for their disclosures of technology and various sensor arrangements.

It would be an improvement to provide a precision fluid interrogation device that is capable of metering very precise quantities of a fluid to form a sample, and electrically interrogating that sample to determine one or more characteristic, such as particle count per unit volume. It would be a further advance for the apparatus to be embodied as a low-cost, one-time-use, rugged, and disposable device.

DISCLOSURE OF THE INVENTION

The present invention provides an apparatus and method for extracting a fluid sample from a bulk container of fluid. Currently preferred embodiments are operable to perform certain tests on one or more portion of the fluid sample, such as particle count per unit volume, and/or may verify a volumetric size or flow rate of the sample, or a portion thereof, among other functions.

A currently preferred embodiment forms a pipette tip having an elongate body stretching between a proximal end and a distal end with a fluid path through the body extending from the distal end toward the proximal end. The preferred embodiment includes a sensor component disposed to electrically interrogate fluid flowing along the fluid path. Desirably, embodiments of an operable sensor component are configured and arranged to determine volumetric particle count. Sometimes, the sensor component may be configured and arranged to determine a fluid flow rate along the fluid path. Optionally, the sensor component may be configured and arranged to detect the presence of a fluid boundary edge at a particular location along the fluid path.

In some cases, the body is structured to include a plurality of layers configured and arranged to provide at least a portion of the fluid path. In such cases, a workable sensor component includes a first electrically conductive trace carried between first and second adjacent layers, with at least a first portion of the first trace being disposed to contact fluid flowing along the fluid path. In certain cases, a second electrically conductive trace may be carried between adjacent layers, with at least a second portion of the second trace being disposed to contact fluid flowing along the fluid path. Sometimes, the first portion and the second portion are spaced apart along the fluid path and carried between the same layers. Other times, the first portion and the second portion are spaced apart along the fluid path and carried between different layers.

In certain embodiments, part of the fluid path is defined by a length of lumen encompassing a known volume. Further, the first portion can be disposed relative to the length of lumen effective to indicate passage through the pipette tip of an amount of fluid comprising a sample volume corresponding to that known volume.

Some embodiments may include structure adapted to permit detection of the tip when the tip is installed in a pipette. The pipette tip may be used to advantage in combination with a pipette that is configured and arranged to couple with the proximal end of the pipette tip. Desirably, coupling the tip to the pipette is effective to permit application of suction to a proximal portion of the fluid path. Furthermore, it is desirable for the act of coupling the tip and pipette to place the sensor component in-circuit with electrical interrogation apparatus.

A device may be used by coupling a pipette tip structured according to certain principles of the instant invention to a cooperatingly structured pipette effective to place the sensor component into electrical communication with electrical interrogation apparatus, and to place a proximal end of the fluid path in communication with a suction source. Then, a fluid-motive pressure is applied effective to draw a sample into the pipette tip. At least a portion of the sample is electrically interrogated as that portion flows along the fluid path and past the sensor component. Data collected by the sensor component may be shown on a display screen associated with the pipette, and/or transferred to a computer for further analysis or storage. Subsequent to completion of fluid sample analysis, the used pipette tip is discarded.

A preferred method of applying suction encompasses generating an excess suction pressure that may then be down-regulated by structure associated with the pipette effective to apply: i) a first suction pressure operable to draw a sample into the pipette tip; and ii) a subsequent desired suction pressure profile over time.

These features, advantages, and alternative aspects of the present invention will be apparent to those skilled in the art from a consideration of the following detailed description taken in combination with the accompanying drawings.

BRIEF DESCRIPTION OF THE DRAWINGS

In the drawings, which illustrate what are currently considered to be the best modes for carrying out the invention.

MODES FOR CARRYING OUT THE INVENTION

Reference will now be made to the drawings in which the various elements of the invention will be given numerical designations and in which the invention will be discussed so as to enable one skilled in the art to make and use the invention. It is to be understood that the following description is only exemplary of the principles of the present invention, and should not be viewed as narrowing the claims which follow.

As typically used in this disclosure, and unless otherwise obvious in context, the term "fluid" may include a liquid alone, one or more liquids in a mixture, or one or more liquid and particles entrained or suspended therein. Desirably, a fluid will have electrolytic properties.

The term "particle" and its variants, is intended to encompass a small piece of matter, nonexclusively including a live or dead biological cell, and a molecule.

Unless otherwise apparent in context, "pressure" and "suction" is intended to be measured with respect to local atmospheric pressure.

Figure 1:
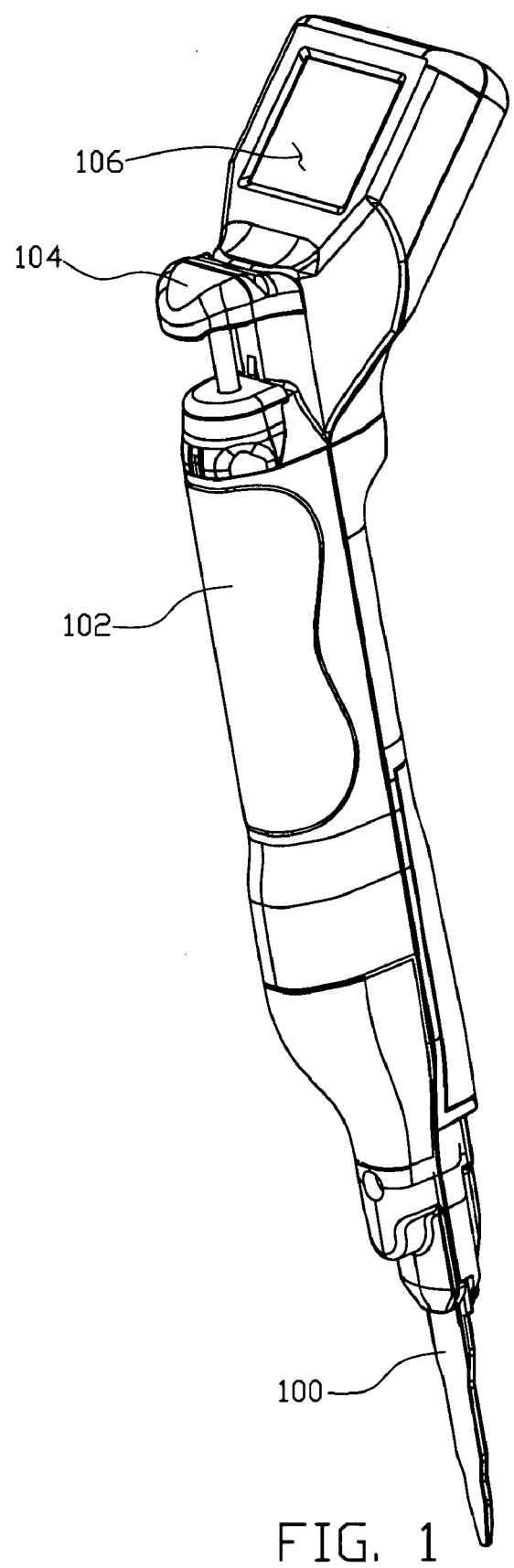
FIG. 1 is a view in perspective of a pipette and installed pipette tip.

A pipette tip may be defined as a removable extension conduit forming a bridge for sample fluid flow from a bulk fluid source toward a pipette. A pipette tip includes a typically slender body into which a small amount of fluid is suctioned for transfer, measurement, or analysis. A proximal end of a pipette tip is structured for removable attachment to cooperating anchor structure of a pipette. A distal end of a pipette tip is structured for its reception inside a sample container having a typically small-sized opening, such as a test tube. An exemplary pipette tip 100 is illustrated in FIG. 1.

A pipette is defined as an instrument or device that is adapted to couple with, and draw a sample of fluid into, a pipette tip. The pipette is structured to apply a vacuum to the proximal end of a pipette tip. A pipette may be hand-held, such as pipette 102 illustrated in FIG. 1. Pipette 102 includes a thumb-operated plunger 104 and a display screen 106. Alternatively, a pipette may be embodied as a bench-top device, such as pipette 108 illustrated in FIG. 12. In any case, a pipette typically is used to obtain one or more fluid sample, with each sample having a repeatable size ranging from less than 1 µl, to several µl, to perhaps 1,000 µl, or more.

A currently preferred pipette tip is indicated generally at 110 in FIGS. 2 through 6. Pipette tip 110 is structured to extract a fluid sample from a bulk fluid container that has a relatively small access opening, such as a 1.5 ml vial. Pipette tip 110 includes a body 112 that is structured to draw fluid along a fluid path extending from a distal end 114 toward a proximal end 116. In general, fluid may be urged to flow though the body 112 by applying a fluid-motive pressure differential to the fluid path. Typically, the fluid-motive pressure is caused by application of a low pressure (or suction) to a proximal portion of the fluid path. Pipette tip 110 includes a suction orifice 118 that is in communication with a proximal portion of the fluid path through body 112 (see FIG. 4). Suction is generally applied to orifice 118 by a pipette, such as pipette 102 or 108.

Pipette tip 110 includes a plurality of electrical contact pads, generally 120, that are carried on proximal end 116. As will be explained in more detail below, such contact pads are visible portions of electrically conductive traces, which have been patterned and extend to various locations through the body 112. Desirably, at least a portion of at least one such trace is disposed to contact fluid flowing along the fluid path in the body 112. Such construction places a sensor component (e.g. the wetted portion of the trace) in the fluid path effective to electrically interrogate fluid flowing along the fluid path.

Figure 2:
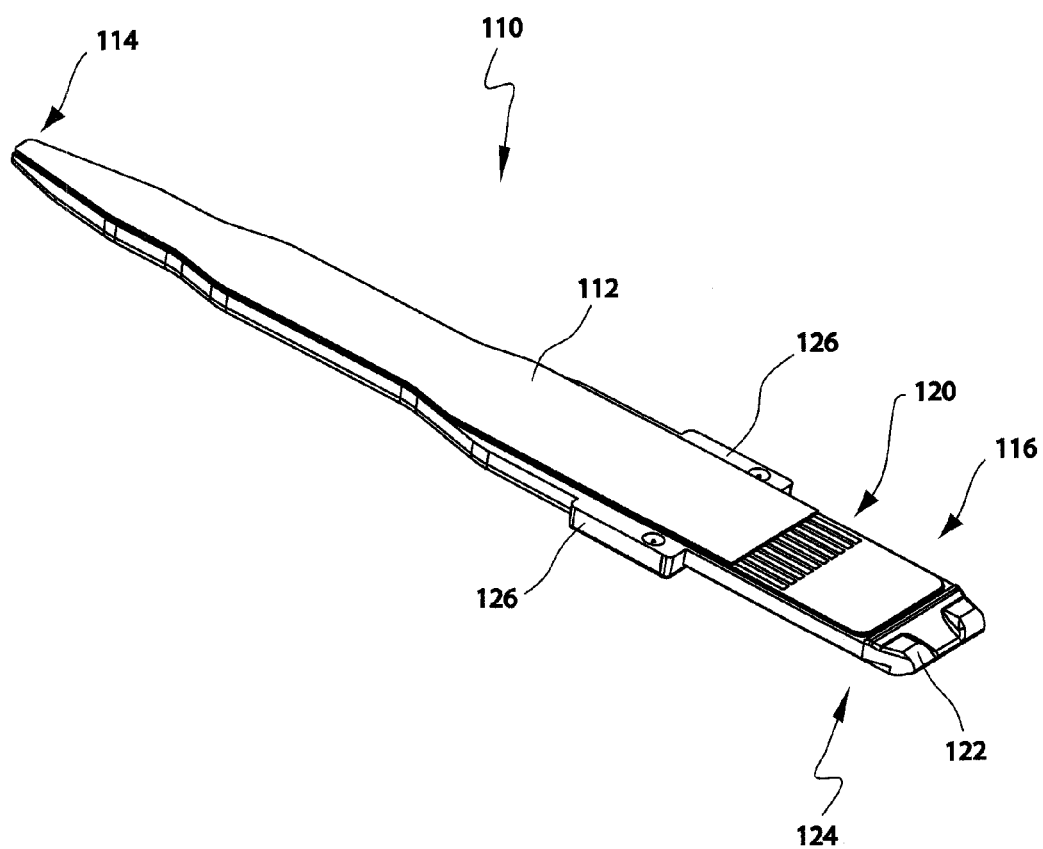
FIG. 2 is a view in perspective of a currently preferred pipette tip.
Figure 3:
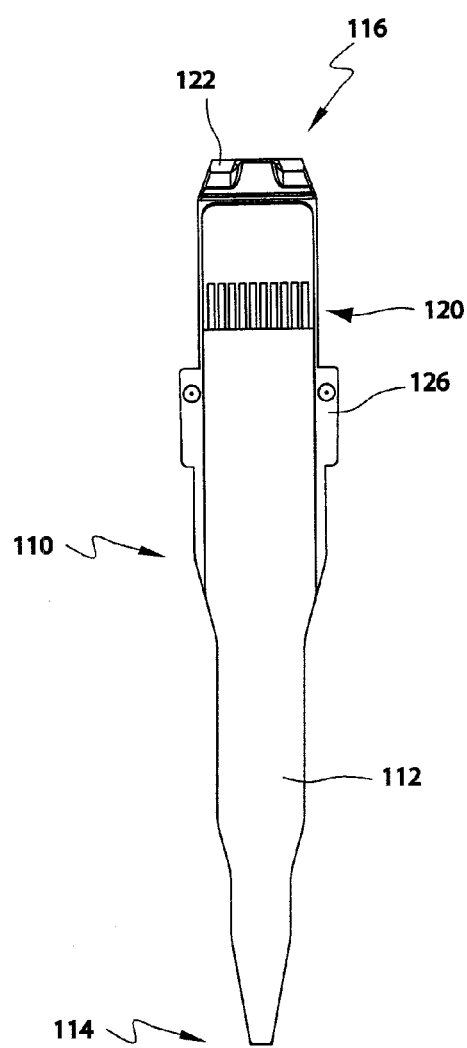
FIG. 3 is a top plan view of the pipette tip illustrated in FIG. 2.

Desirably, structure disposed at the proximal end of body 112 is configured and arranged in harmony with coupling structure of a pipette such that the tip 110 may be installed only in an operable orientation. With reference to FIG. 2, illustrated proximal end 116 forms a tongue that may be engaged inside a cooperatingly formed receiving socket of a pipette. As illustrated in FIGS. 2 and 3, shoulders 122 disposed near the proximal end 116 of body 112 are structured to form a rabbet 124. The cross-section of the proximal end 116 thereby fits into reception in a cooperatingly formed receiving socket of a pipette only in the desired orientation. Insertion of proximal end 116 into the receiving socket places a suction source associated with the pipette into communication with orifice 118. Also, installing tip 110 in a pipette desirably places electrical contacts of an electrical connector into operable communication with contact pads 120. A proximal portion of wing 126 is structured as a stop to limit insertion depth of the tip 110 into the pipette's receiving socket.

Figure 5:
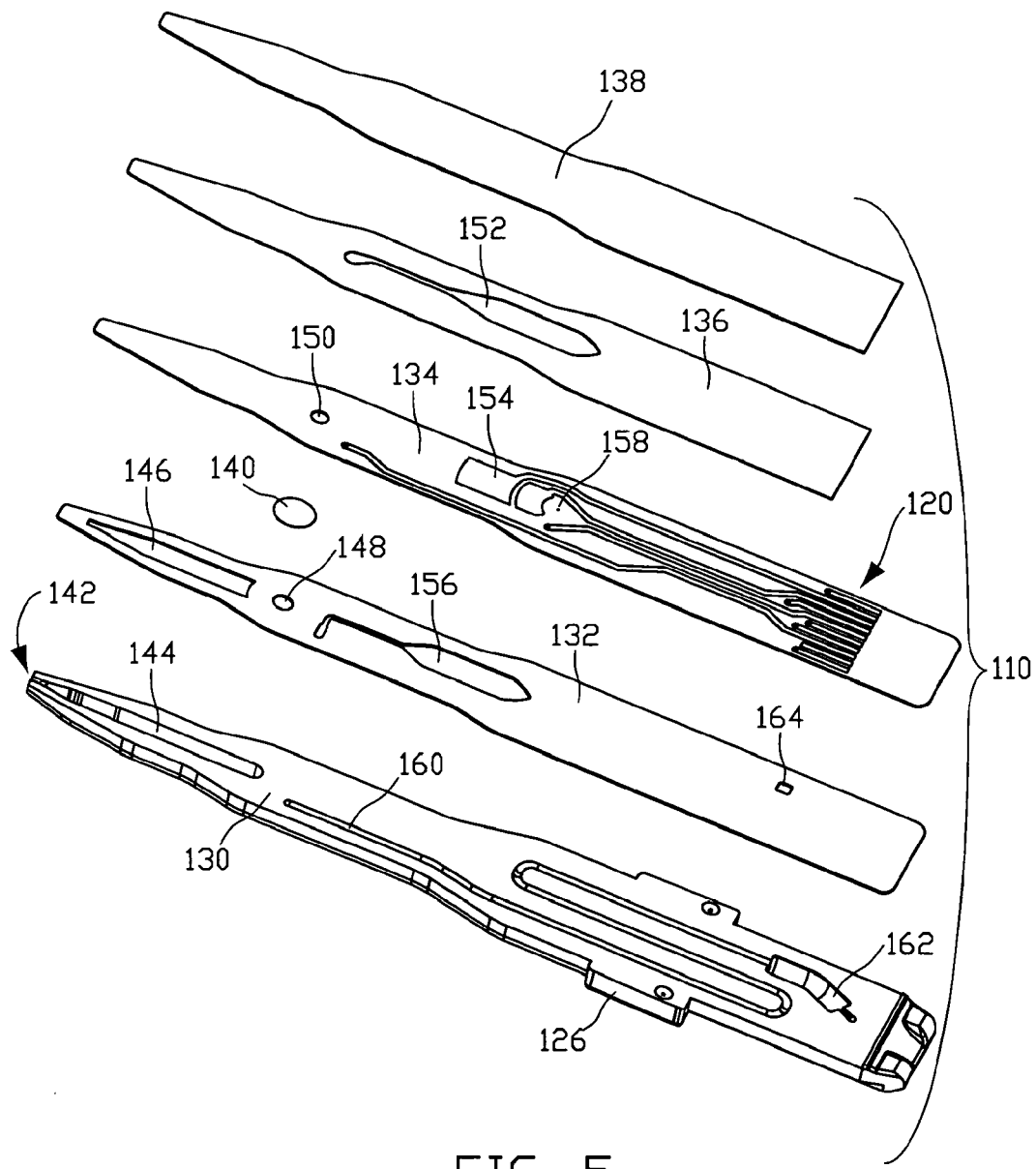
FIG. 5 is an exploded assembly view from above of the pipette tip illustrated in FIG. 2.
Figure 6:
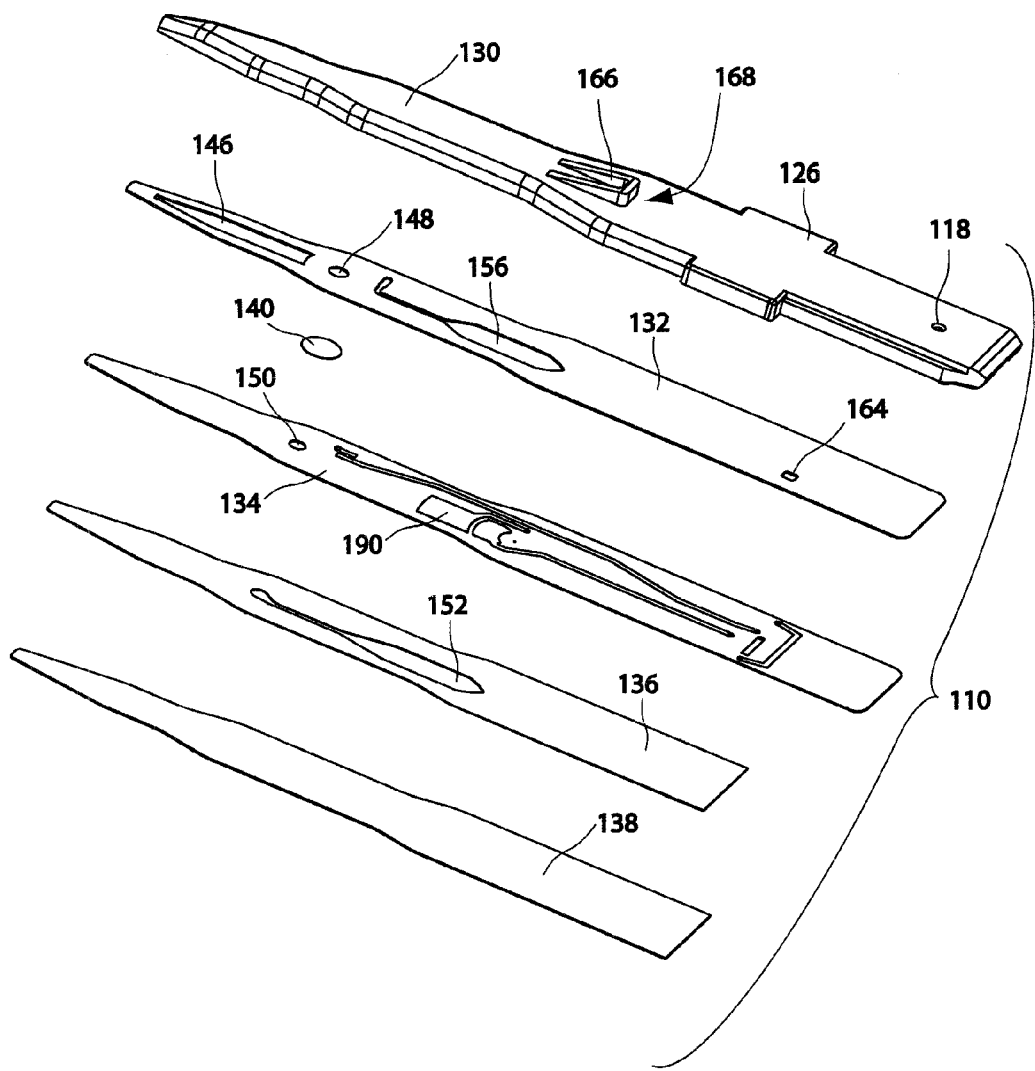
FIG. 6 is an exploded assembly view from below of the pipette tip illustrated in FIG. 2.

With reference now to FIGS. 5 and 6, it can be seen that an operable pipette tip 110 includes a plurality of layers. Illustrated base layer 130 is injection molded from medical grade plastic. Channel layer 132 is formed from double-sided adhesive polyester tape. Substrate layer 134 is formed from polyester film. Channel layer 136 is formed from double-sided adhesive polyester tape. Cap layer 138 is formed from polyester film. Sometimes, a filter, such as illustrated filter 140, may be included. Illustrated filter 140 is a nylon net filter with 30 micron pores, and is used in certain pipette tips that are used in application to blood cell interrogation.

Pipette tip 110 includes a distally opening sample orifice, generally 142 disposed at the distal tip of pipette tip 110. While the orifice 142 is illustrated as being disposed only in base layer 130, it is within contemplation that the distal opening 142 may be formed by a channel disposed in one or more layers. As illustrated, orifice 142 is typically disposed on the edge of the tip 110. An alternative operable sample opening may be structured to have a transverse opening through a side of the pipette tip. In any case, orifice 142 permits a fluid sample to be drawn into distal chamber 144. An optional distal channel 146 disposed in layer 132 may be provided to augment a volume of distal chamber 144.

The proximal end of chamber 144 communicates through aperture 148, filter 140, and aperture 150, to a distal portion of channel 152. Channel 152 is configured to cause inspired sample fluid to flow over one or more surface electrode, such as stimulated electrode 154. A proximal portion of channel 152 communicates with a proximal portion of channel 156 by way of interrogation aperture 158. Channel 156 also is configured to cause inspired sample fluid to flow over one or more surface electrode. A distal portion of channel 158 communicates fluid to a distal portion of channel 160. Fluid may then be drawn along channel 160 toward receiving chamber 162. Suction applied to suction orifice 118 communicates with chamber 162, and provides a fluid motive force effective to urge fluid flow from a bulk container, into the sample orifice 142, and toward chamber 162. A window 164 is provided in channel layer 132 to permit fluid near the proximal end of channel 160 to contact a surface electrode carried on the bottom of substrate layer 134.

Figure 4:
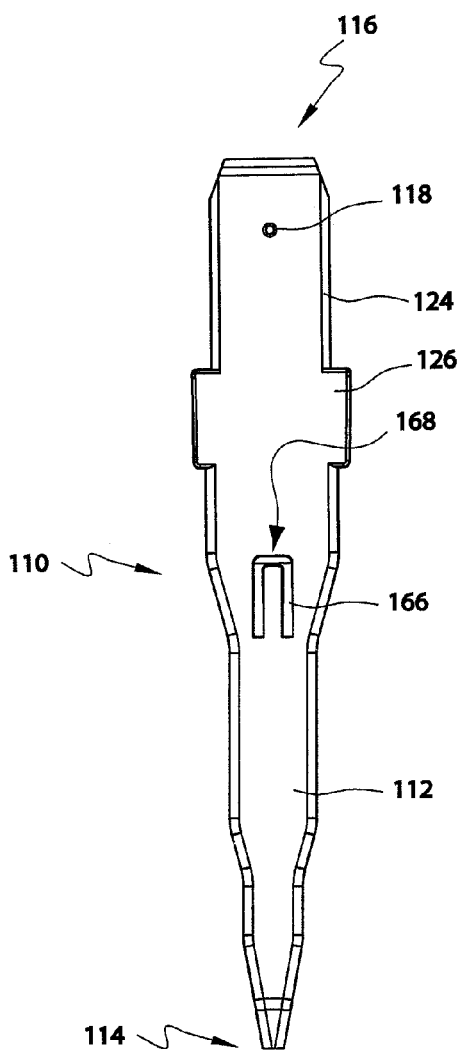
FIG. 4 is a bottom plan view of the pipette tip illustrated in FIG. 2.

Sometimes, and as illustrated in FIGS. 4 and 6, a pipette tip may include extraction structure configured to assist in removal of the tip from coupled registration with a pipette. As one example, a ramp 166 may be included in a tip 110 to provide a catch surface, generally indicated at 168, against which tip-removal structure can be pressed to impart an axially oriented removal force into the tip 100.

Figures 7, 8:
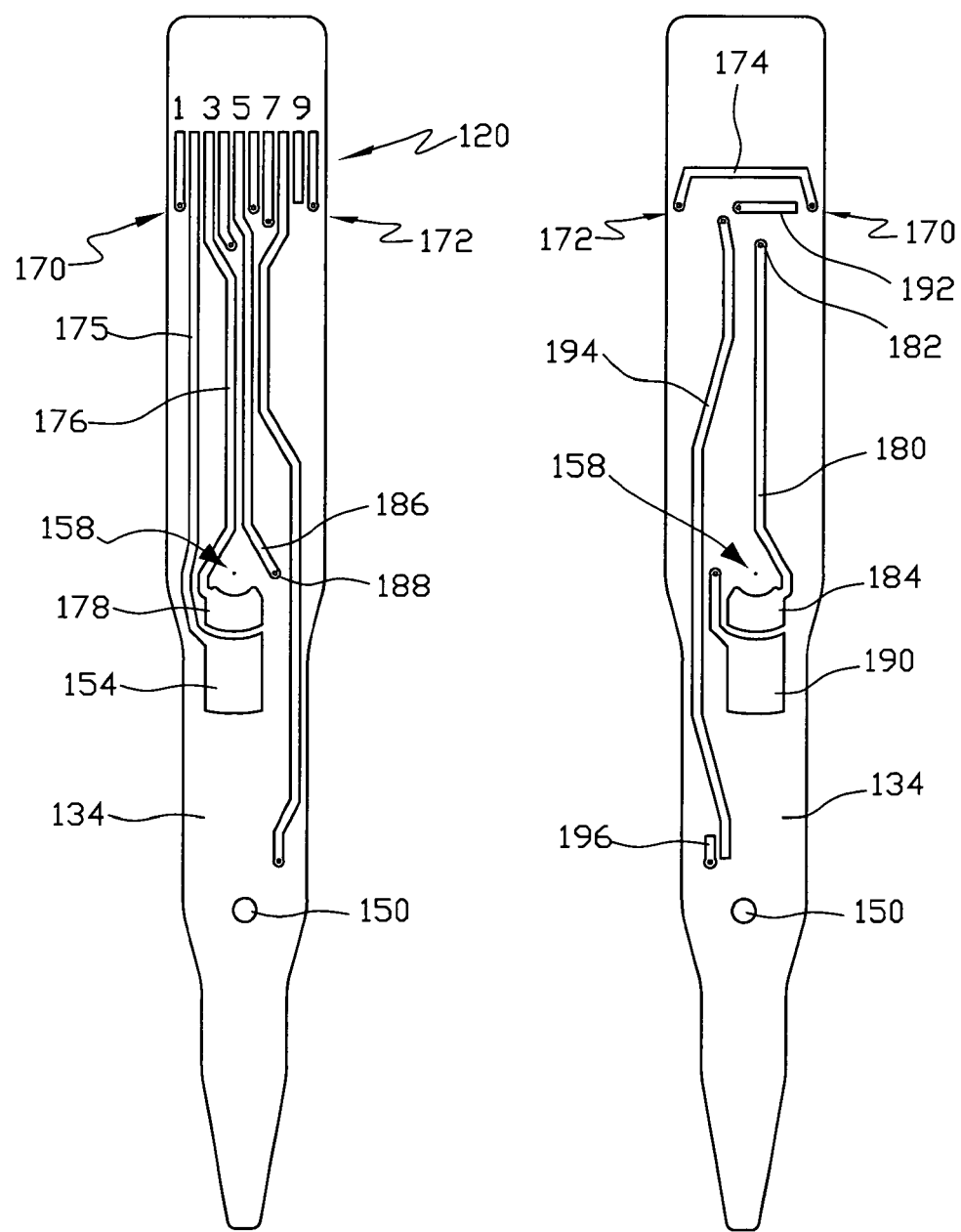
FIG. 7 is a top plan view of a substrate portion of the pipette tip illustrated in FIG. 2.
FIG. 8 is a bottom plan view of a substrate portion of the pipette tip illustrated in FIG. 2.

With reference now to FIGS. 7 and 8, a plurality of electrically conductive traces are patterned on top and bottom surfaces of the substrate 134. In the illustrated embodiment, the proximal ends of the electrically conductive traces form ten electrical contact pads, indicated generally at 120, and odd pads of which are numbered 1, 3, 5, 7, and 9. It is currently preferred for all of the contact pads to be disposed on a single side of substrate 134, and in a configuration disposed in agreement to couple with a commercially available ten-pin electrical connector. Of course, the number and arrangement of traces will depend upon a desired capability for the resulting pipette tip.

Note that vias, such as generally indicated at 170 and 172, are provided to permit certain contact pads to communicate through-the-thickness to electrodes and/or trace elements that are disposed on the opposite side of the substrate 134. Vias may be regarded as holes formed in the substrate 134. Conductive material, such as the currently preferred conductive ink, which is applied in a desired pattern to each side of the substrate 134, forms an electrical connection extending through the via (from one side to the other of the substrate 134).

Trace element 174 is disposed on the bottom of substrate 134, basically as a jumper, to place contact pad number 1 into fixed electrical communication with contact pad number 10. Such an arrangement can be used to provide a feedback signal for various uses, such as to permit verification of correct installation of the tip 110 into seated registration with a pipette, such as pipette 102. It is within contemplation that the pipette may detect the pipette tip based upon such feedback, and can then run a selected test based upon the type of tip that is detected. For example, an electrical continuity test between various individual contact pads can be used to distinguish between several different trace configurations of pipette tips having the 10-pin contact pad arrangement 120. In the illustrated case, electrical continuity between contact pads 1 and 10 can also be used to indicate that the pipette 110 is configured as a particle counter, among other uses. In the case where a different pipette tip is structured e.g. only to precisely measure fluid quantities of one or more serially-dispensed or inspired sample, the trace element 174 could be left off, or used as a connector between different contact pads to provide a different electronic "signature".

A proximal portion of trace element 175 forms contact pad number 2. A distal portion of trace element 175 forms stimulated electrode 154. A proximal portion of trace element 176 forms contact pad number 3. A distal portion of trace element 176 forms detection electrode 178. Electrodes 154 and 178 are configured to dispose relatively large surface areas in contact with fluid flowing through channel 152 (see FIG. 5).

A proximal portion of trace element 180 forms contact pad number 4. Trace element 180 communicates between the top and bottom surface of substrate 134 through via 182. A distal portion of trace element 180 forms detection electrode 184. A proximal portion of trace element 186 forms contact pad number 5. Trace element 186 communicates between the top and bottom surface of substrate 134 through via 188. A distal portion of trace element 186 forms stimulated electrode 190. Electrodes 184 and 190 are configured to dispose relatively large surface areas in contact with fluid flowing through channel 156 (see FIG. 6). The large surface areas of certain electrodes, such as electrodes 154 and 190, permits application of an electric signal to the corresponding contact pads to obtain a desired current flow between such electrodes.

A proximal portion of trace element 192 forms contact pad number 6. A distal portion of trace element 192 (disposed on the bottom of substrate 134) forms a surface electrode that is disposed to detect a fluid front, such as the leading, or trailing, edge of a column of electrolyte traveling along channel 160. Detection of the change in a signal at an electrode can be used to determine the location of the fluid boundary at a point in time. Such information may be used in combination with a known volume, through which the fluid has been inspired, to determine fluid flow rate. The boundary location information may also be used to verify extraction of a desired volume, or to check for air bubbles in a sample.

In a simple arrangement, an instrumented pipette tip may include a single electrode disposed at a known location in a fluid flow channel through the tip. An electric signal may be applied to a bulk container of electrolytic fluid. The fluid may be inspired into the instrumented pipette tip, and a position of the leading edge of the fluid can be detected by monitoring the signal at the electrode. Once the column of electrolyte reaches the electrode, a signal may be detected at that electrode. The signal obtained at the electrode can be used as a trigger event, such as to start a test procedure, or to stop inspiring fluid.

A proximal end portion of trace element 194 forms contact pad number 7. A proximal end portion of trace element 196 forms contact pad number 8. Contact pad number 9 is not electrically functional in the illustrated pipette tip 110. Distal portions of trace element 194 and 196 are disposed as surface electrodes effective to determine presence of a fluid boundary at locations spaced apart along the distal portion of channel 156. The volume encompassed by channel 160 and disposed between electrodes 192 and 194 may be defined to correlate with a desired fluid sample size.

Figure 9:
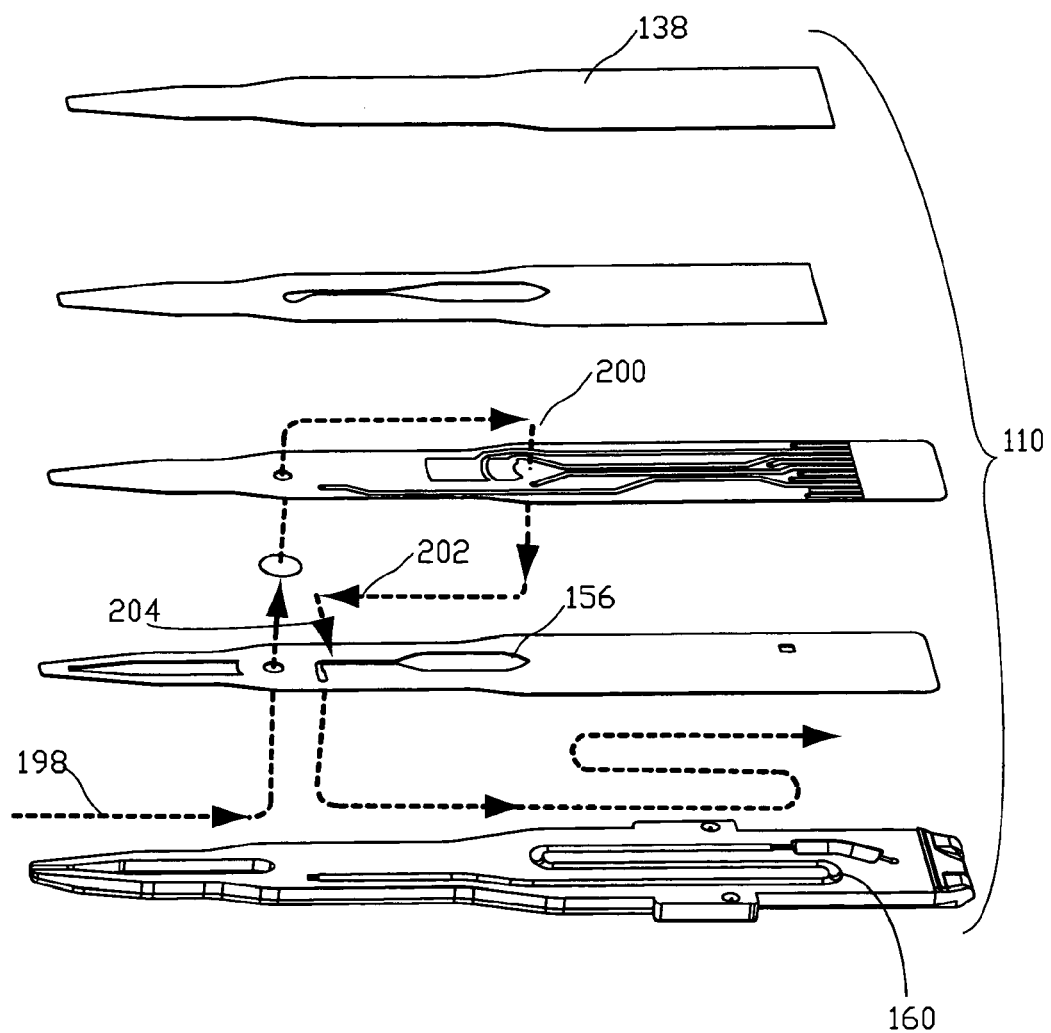
FIG. 9 is an exploded side view of the pipette tip illustrated in FIG. 2.

The fluid flow path through a pipette tip 110 is approximated as a series of dashed lines that indicate different stretches of fluid flow in FIG. 9. In contrast to the substantially unidirectional fluid flow in a conventional pipette tip, the flow path through pipette tip 110 follows a tortuous route. For certain embodiments of pipette tips structured according to certain principles of the instant invention, it can be said that the centerline axis of fluid flow along the tortuous route defines a 3-dimensional space. That is, at various times, fluid may flow in a length direction, in a width direction, in the thickness direction, or some combination thereof. For example, fluid flow along channel 144 and indicated by stretch 198 is in a proximal (and length) direction. Fluid flow through the interrogation aperture 158 and indicated by stretch 200 is in a transverse (and thickness) direction. Fluid flow along the bulk of channel 156 and indicated by stretch 202 is in a distal (and length) direction. Fluid flow at the distal portion of channel 156 and indicated by stretch 204 is in a generally transverse (width) direction, as is flow through the gooseneck portions of channel 160.

Figure 10:
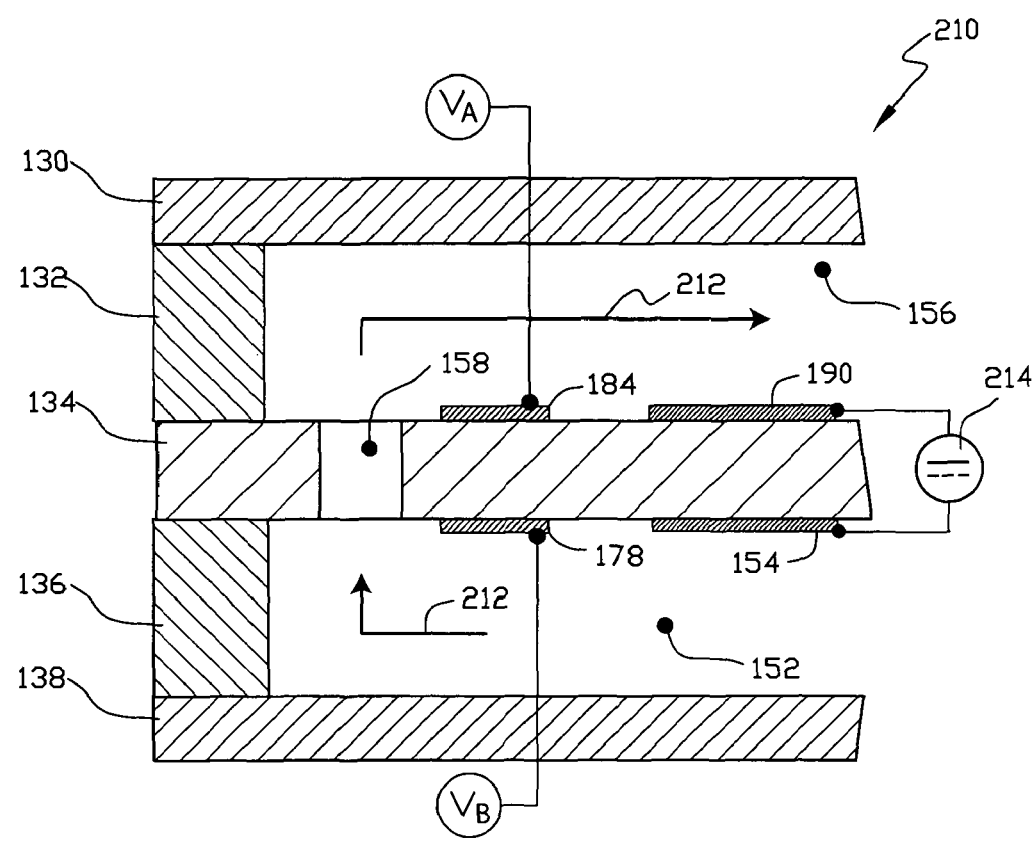
FIG. 10 is a cross-section view of structure that may be present in certain pipette tips structured according to certain principles of the instant invention.

A cross-section schematic of a currently preferred arrangement operable to detect and count particles entrained in a fluid is illustrated in FIG. 10, and is generally indicated at 210. A fluid flow path 212 is formed as a channel structure formed by fluid-confining voids within layers. Desirably, at least for certain embodiments, the through-hole, or interrogation aperture 158, is sized to urge particles that are entrained in an electrolytic fluid flowing there-through into substantially single file. The interrogation aperture 158 typically has a characteristic size (diameter) between about 50 nanometers and 200 microns in certain pipette tips 100 that are used to interrogate whole blood. As illustrated in FIG. 10, a pair of cell-counting electrodes 178 and 184 are disposed on opposite sides of the through-hole 158. Cooperating stimulated electrodes 154 and 190 are also disposed (one upstream and one downstream) on opposite sides of the through-hole to form a 4-electrode interrogation zone encompassing the interrogation aperture 158.

As illustrated, it is currently preferred for the detection electrodes to be configured in such a way as to ensure their complete wet-out as the fluid flows along the flow path 212. That is, the electrodes 178 and 184 are "pulled back", along the flow path from aperture 158. The illustrated configuration resists changes in signal amplitude or quality as the wetted area of the electrode changes, perhaps due to presence of a bubble over a portion of the electrode.

In use of the illustrated device 210 to detect and count particles, a constant-current time-dependent signal can be applied by a signal generator 214 to stimulated electrodes 154 and 190. The stimulated electrodes are desirably sized to present a significant wetted surface area to facilitate driving an electric current into the fluid and interrogation zone 158.

Detecting, or counting electrodes 178 and 184, are disposed in-circuit to measure the differential voltage change across the interrogation hole 158.

It is within contemplation alternatively to form a 2-electrode, or 3-electrode interrogation zone. For example, one or the other of detection electrodes 178 and 184 may alternatively be placed in-circuit to detect changes in a signal measured relative to one of the stimulated electrodes disposed on the other side of the interrogation aperture 158, or relative to ground. It should be noted that an applied electrical signal (e.g. applied by signal generator 214) may be substantially constant (DC) or time dependent (AC), depending upon a desired piece of data to be obtained.

Detection electrode 178 may be considered to be a surface electrode that contacts fluid on only a portion of the perimeter of the flow path of a channel passing over a portion of its surface area. It is further within contemplation alternatively to form an interrogation zone having thickness electrodes disposed, e.g. to form the entire perimeter of the fluid flow channel or path. Such electrodes may be disposed in series along the flow path. For example, a pair of surface electrodes may be disposed on opposite sides of a first substrate. Additional surface electrodes can be carried by one or more additional substrate, an insulating spacer may be provided between adjacent such electrodes, and a plurality of substrates can be stacked and bonded together to arrange a laminated collection of surface electrodes in transverse series. An interrogation aperture 158 may then be drilled transversely through the stacked electrodes and insulating layers to form an interrogation zone (or drilled conduit) having a plurality of thickness electrodes disposed along its length.

Figure 11:
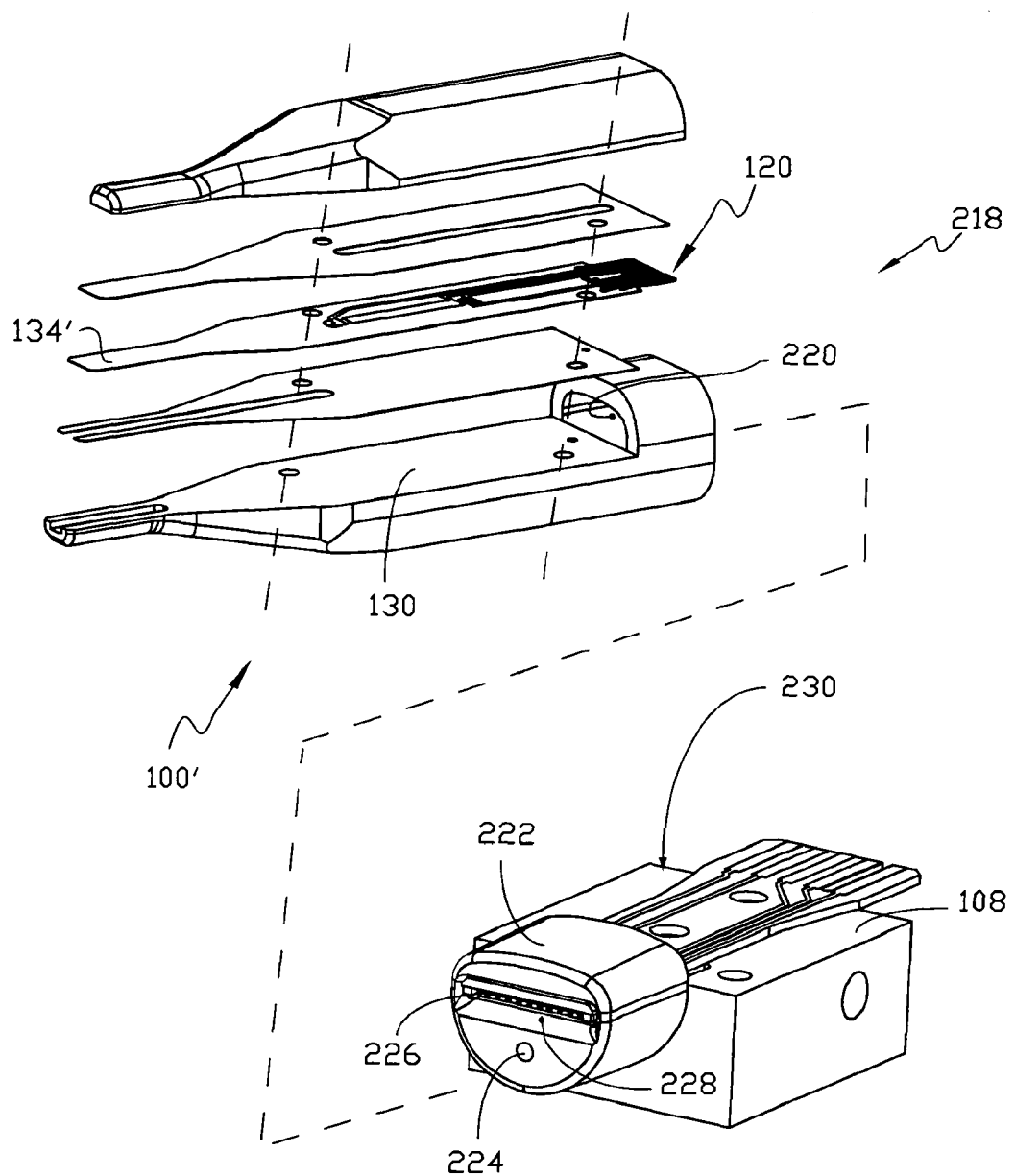
FIG. 11 is an exploded assembly view of a pipette tip and an exemplary bench-top pipette.

A pipette tip 100', having mounting structure with a different configuration, generally indicated at 218, is illustrated in FIG. 11. Mounting structure 218 includes a socket 220 affixed to base layer 130. Socket 220 is configured in harmony with tongue 222 of bench-top pipette 108 to permit coupling the tip 100' in fluid communication with suction port 224. Engaging socket 220 and tongue 222 also places contact pads 120 into electrical communication with edge connector 226. The proximal end of substrate 134' is adapted for insertion into slot 228 to effect an electrical connection for communication between a sensor component carried by tip 100' and interrogation apparatus 230 associated with the pipette 108.

A representative method for using a pipette tip, such as pipette tip 110, includes installing the pipette tip 110 by inserting its proximal end into cooperating receiving structure of a pipette, e.g. pipette 102 in FIG. 1. Pipette 102 is structured to couple a fluid-motive pressure source (suction) to the orifice 118 of an installed tip 110. Installing the tip 110 in the pipette 102 also places an electrically-based sensor of the tip 110 in communication with electrical interrogation apparatus associated with the pipette 102. The distal end 114 of tip 110 is dipped into a bulk fluid container, such as a 1.5 ml vial, and a sample is extracted to begin analysis of the fluid. Subsequent to completion of the analysis, the tip 110 is discarded. For purpose of this disclosure, the term "analysis" is intended to include one or more of: inspiring or dispensing one or more volume, detecting and/or counting particles, determining sample flow rate, and the like. Typically, data gathered from the sensor component is manipulated and indicated on the display 106, and may be transferred to a computer for further analysis or storage.

A preferred pipette 102 is capable of generating an excess suction by simply depressing the plunger 104. The excess suction may then be down-regulated (e.g. by electronics, one or more pressure transducer, and valve structure associated with the pipette 102), to apply a desired pressure profile over time to the orifice 118. A representative pressure profile for one useful test is illustrated in FIG. 12.

Figure 12:
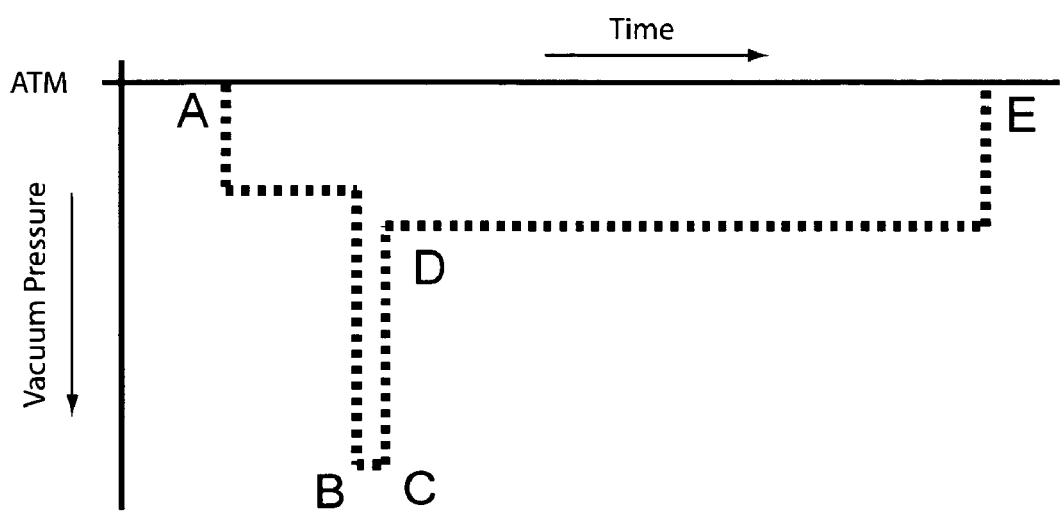
FIG. 12 illustrates a desirable applied (suction) pressure profile during an exemplary use of one embodiment structured according to certain principles of the instant invention.

With reference to FIG. 12, at A, a relatively low suction pressure (e.g. about 10" of water) is applied to a submerged pipette tip 114 to draw a complete fluid sample into the tip 110 during the time increment between A and B. Under many circumstances, the fluid sample will stop on its own at the cell detection zone (aperture 158) due to surface tension in the small hole. Alternatively, feedback from an electrode may be used to determine complete sample acquisition. Over the time increment between B and C, a brief vacuum spike (e.g. about 30" water) is briefly applied to draw the fluid through the interrogation hole 158. Typically, the pressure for the duration of the test (from D to E) is reduced and desirably held substantially constant (e.g. at a value selected from between about 1-25 psi depending on the hole size, carrier fluid, and particle(s) to be interrogated, among other variables). A representative time increment during which a sample is loaded into one embodiment of a pipette tip 110 is about 5 seconds or less. A representative time increment over which the vacuum spike is applied is about 1 second. That said, the vacuum spike is not always needed. It may be possible to do this with a minimum of even a single vacuum setting. A desirable vacuum profile depends, in part, on the size of the detection sensor hole 158 being used. Larger holes 158 may not require spikes, etc.. The data acquisition stage of a particle-counting test on a particular representative particle suspension sample takes about 30 seconds.

Currently preferred pipette tips, structured similarly to pipette tip 110, use about 25 microliters as the sample size. It is within contemplation to also provide pipette tips capable of analysis of samples having either smaller (including much smaller) or larger size. One pipette tip contemplated for use in particle analysis may inspire 50 microliters, or even much more. Bigger sample size generally means even more precision (a plus) but more sample (often, a minus).

An operable pipette tip 100 may be manufactured using pick-and-place, or reel-to-reel techniques. It is currently preferred for the electrically insulating layers to be formed from flexible, film-like plastic materials, including polyamides and polyesters such as Mylar and Kapton, respectively. Channels, such as channel 156, may be die cut, or machined by water jet or laser. Electrically conductive traces are applied to desired portions of one or more layer. The interrogation aperture 158 of a currently preferred pipette tip 100 is laser drilled through the substrate 134 prior to assembly of adjacent layers. Layers are typically stacked in registration, and bonded together. In mass production, individual assembled pipette tips 100 may be die-cut from a bulk laminated sheet or length of laminated tape. Certain operable Polyester films are commercially available from Dupont Teijin.

The electrically conductive trace elements may be formed from metal or alloys of metals, including Aluminum, Platinum, Gold, Copper, Silver, Chromium, Titanium, and the like, although any other operable electrically conductive material would suffice. It is currently preferred to apply the trace elements onto an electrically insulating film substrate to improve material handing characteristics during assembly of the pipette tip. Application of a trace element to a carrying layer may be carried out by electroplating, or using some other known deposition method, such as screen printing techniques, ink jet technology, laser etching, sputtering or electrodeposition techniques, and the like. Micro-machining methods, such as masking and etching may also be used to formulate individual conductive trace element structures.

In a currently preferred manufacturing method, through-the-thickness vias are pre-formed in the substrate, and the electrodes are then printed to form an electrically conductive path through such vias. Typically, a trace is first printed on one surface of a substrate. Then, the substrate is reprinted from the backside, carefully controlling how the ink exits any via (hole) to prevent unwanted connection between traces. As the ink flows through the via from each side and dries, an electrical connection is made. The silk screen causing the trace pattern is removed after printing, and the substrate is typically placed in a dryer. The ink is generally cured (at least to some degree) prior to back side printing. Through-vias are currently drilled with a laser (although they can be formed using other techniques such as with a steel rule die, punch dies, and rotary dies, etc.). Printed panels are generally dried after each print step in an industrial dryer. Some printed inks are cured with UV light. Screen printing for high volume manufacturing can occur in a web-type, roll format or sheet feed type applications.

An operable conductive ink includes a Silver/Silver Chloride solution, such as Dupont 5870 Ag/AgCl. Certain other operable inks are set forth on the world wide web at http://www2.dupont.com/MCM/en_US/PDF/biosensor-H9156101.pdf. Similar printable electrically conductive inks are available from Conductive Technologies, having a web site located at http://www.conductivetech.com. Line widths forming a trace element, and spacing between trace elements, of about 0.2 mm are possible. It is generally preferred that width and spacing not be smaller than 0.3 mm for most applications. Thickness of deposited material is controlled, to large degree, by thickness of the silk screen itself.

The thickness of the four thin film layers in currently preferred pipette tips used to interrogate certain fluid samples, including particles in suspension in a carrier liquid, is about 0.005 inches thick each. More or fewer layers, and a mix of layers having different thicknesses, are within contemplation. Each layer could potentially be constructed using films of between perhaps about 0.0005 inches and 0.035 inches in thickness, or so. An operable range of thickness for certain electrodes used for particle detection or characterization is between about 0.1 microns (0.000004 inches) and about 127 microns (0.005 inches), or so. The stimulated electrodes 154, 190 used in particle detection/counting are typically arranged to have a relatively large surface area (e.g. 70 $cm^2$) disposed in contact with the sample solutions (which keeps the electrode/electrolyte interface impedance low). The characteristic size (diameter) of the interrogation aperture is about 50 microns. The length of the interrogation aperture (e.g., 127 microns) to diameter ratio may be important for certain particle characterization procedures, and is currently maintained at approximately 2.5. The ratio of channel depth-to-width is partially determined by tape thickness being used, and is not generally an important design driver.

It is within contemplation to provide surface coatings on sensors structured according to certain principles of the instant invention to reduce impact from contact with the sensor structure and the fluid passing therethrough. Such coating arrangement can be provided to reduce the clotting cascade in whole blood samples, for example. Coatings operable in sensors for use with such blood samples include Teflon, heparin, and PRO-based materials.

While the invention has been described in particular with reference to certain illustrated embodiments, such is not intended to limit the scope of the invention. The present invention may be embodied in other specific forms without departing from its spirit or essential characteristics. For non-limiting examples, a layer may have a non-flat conformation, and may only extend along only a portion of the length of a pipette tip. The described embodiments are to be considered only as illustrative and not restrictive. The scope of the invention is, therefore, indicated by the appended claims rather than by the foregoing description. All changes which come within the meaning and range of equivalency of the claims are to be embraced within their scope.

What is claimed is:

1. In a pipette tip of the type used to extract a sample from a container of fluid, the pipette tip including an elongate body stretching between a proximal end and a distal end with a fluid path through the body extending from the distal end toward the proximal end, the improvement comprising:
 a sensor component disposed to interrogate fluid flowing along said fluid path effective to determine information about said sample, wherein:
 said body comprises a plurality of layers configured and arranged to provide at least a portion of said fluid path; and
 said sensor component comprises a first electrically conductive trace carried between first and second adjacent layers, at least a first portion of said first trace being disposed to contact fluid flowing along said fluid path.

2. The improvement according to claim 1, further comprising:
 a second electrically conductive trace carried between adjacent layers, at least a second portion of said second trace being disposed to contact fluid flowing along said fluid path.

3. The improvement according to claim 2, wherein:
 said first portion and said second portion are spaced apart along said fluid path and carried between the same layers.

4. The improvement according to claim 2, wherein:
 said first portion and said second portion are spaced apart along said fluid path and carried between different layers.

5. The improvement according to claim 1, wherein:
 said sensor component is configured and arranged to facilitate determining volumetric particle count.

6. The improvement according to claim 1, wherein:
 said sensor component is configured and arranged to facilitate determining a fluid flow rate along said fluid path.

7. The improvement according to claim 1, wherein:
 said sensor component is configured and arranged to detect the presence of a fluid boundary edge at a substantially particular location along said fluid path.

8. The improvement according to claim 1, wherein:
 a part of said fluid path is defined by a length of lumen encompassing a known volume; and
 said first portion of said first trace is disposed relative to said length of lumen as part of an arrangement effective to indicate passage through said pipette tip of an amount of fluid comprising a volume corresponding to said known volume.

9. The improvement according to claim 1, further comprising:
 structure adapted to permit detection of said pipette tip when said pipette tip is installed in a pipette.

10. The improvement according to claim 1, in combination with:
 a pipette, said pipette being configured and arranged to couple with said proximal end of said pipette tip effective to:
 permit application of suction to a proximal portion of said fluid path; and
 place said sensor component in-circuit with electrical interrogation apparatus.

11. A method for using the improvement according to claim 1, comprising:
 providing a pipette tip structured according to claim 1;
 coupling said pipette tip to a pipette effective to place said sensor component into electrical communication with electrical interrogation apparatus, and to place a proximal end of said fluid path in communication with a suction source;
 applying said suction source effective to draw a sample into said pipette tip;
 electrically interrogating a portion of said sample as said portion flows along said fluid path; and
 discarding said pipette tip.

12. The method according to claim 11, wherein:
 applying said suction source comprises:
 generating an excess suction pressure that is then down-regulated by structure associated with said pipette effective to apply:
 a first suction pressure operable to draw a sample into said pipette tip; and
 a subsequent desired suction pressure profile.

13. An apparatus, comprising:
 an elongate body comprising a plurality of layers configured and arranged to provide a fluid path extending from at least the vicinity of a distal tip of said body toward mounting structure disposed at a proximal end of said body;
 said mounting structure being configured and arranged in harmony with said body to dispose said distal tip as a free-standing, cantilevered element when said mounting structure is coupled to a device effective to apply a fluid-motive pressure differential to said fluid path; and
 a sensor component disposed in said fluid path effective to electrically interrogate fluid flowing along said fluid path.

14. The apparatus according to claim 13, wherein:
 the distal end of said fluid path communicates through a distally opening sample orifice.

15. The apparatus according to claim 13, wherein:
 said fluid path is a tortuous route comprising:
 a first stretch that is configured and arranged to cause a fluid flow vector to be oriented substantially in a proximal direction; and
 a second stretch that is configured and arranged to cause a fluid flow vector to have a component oriented in a direction transverse to said proximal direction.

16. The apparatus according to claim 15, wherein:
 said tortuous route further comprises:
 a third stretch that is configured and arranged to cause a fluid flow vector to be oriented substantially in a distal direction.

17. The apparatus according to claim 15, wherein:
 the centerline axis of fluid flow along said tortuous route defines a 3-dimensional space.

18. The apparatus according to claim 13, wherein:
 said mounting structure comprises a tongue structured for reception in a cooperating socket of an electrical interrogation device.

19. The apparatus according to claim 13, wherein:
 said mounting structure comprises a socket structured to receive a cooperating tongue of an electrical interrogation device.

* * * * *